US008299025B2

(12) United States Patent
Alessi et al.

(10) Patent No.: US 8,299,025 B2
(45) Date of Patent: *Oct. 30, 2012

(54) SUSPENSION FORMULATIONS OF INSULINOTROPIC PEPTIDES AND USES THEREOF

(75) Inventors: Thomas R. Alessi, Hayward, CA (US); Ryan D. Mercer, Dublin, CA (US); Catherine M. Rohloff, Los Altos, CA (US); Bing Yang, Redwood City, CA (US)

(73) Assignee: Intarcia Therapeutics, Inc., Hayward, CA (US)

(*) Notice: Subject to any disclaimer, the term of this patent is extended or adjusted under 35 U.S.C. 154(b) by 164 days.

This patent is subject to a terminal disclaimer.

(21) Appl. No.: 12/148,896

(22) Filed: Apr. 22, 2008

(65) Prior Publication Data

US 2008/0260840 A1 Oct. 23, 2008

Related U.S. Application Data

(63) Continuation-in-part of application No. 11/347,562, filed on Feb. 3, 2006, now Pat. No. 8,114,437.

(60) Provisional application No. 60/926,005, filed on Apr. 23, 2007, provisional application No. 61/072,202, filed on Mar. 28, 2008, provisional application No. 60/650,225, filed on Feb. 3, 2005.

(51) Int. Cl.
*A61K 38/26* (2006.01)
*A61P 3/10* (2006.01)

(52) U.S. Cl. ............................. 514/7.2; 514/6.8; 514/6.9

(58) Field of Classification Search ........................ None
See application file for complete search history.

(56) References Cited

U.S. PATENT DOCUMENTS

| | | | |
|---|---|---|---|
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,545,618 A | 8/1996 | Buckley et al. |
| 5,574,008 A | 11/1996 | Johnson et al. |
| 5,614,492 A | 3/1997 | Habener |
| 5,728,396 A | 3/1998 | Peery et al. |
| 5,904,935 A | 5/1999 | Eckenhoff et al. |
| 5,932,547 A | 8/1999 | Stevenson et al. |
| 5,958,909 A | 9/1999 | Habener |
| 5,972,370 A | 10/1999 | Eckenhoff et al. |
| 5,997,527 A | 12/1999 | Gumucio et al. |
| 6,029,361 A | 2/2000 | Newman |
| 6,113,938 A | 9/2000 | Chen et al. |
| 6,124,261 A | 9/2000 | Stevenson et al. |
| 6,130,200 A | 10/2000 | Brodbeck et al. |
| 6,132,420 A | 10/2000 | Dionne et al. |
| 6,191,102 B1 | 2/2001 | DiMarchi et al. |
| 6,235,712 B1 | 5/2001 | Stevenson et al. |
| 6,268,343 B1 | 7/2001 | Knudsen et al. |
| 6,270,787 B1 | 8/2001 | Ayer |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,375,978 B1 | 4/2002 | Kleiner et al. |
| 6,451,974 B1 | 9/2002 | Hansen |
| 6,458,924 B2 | 10/2002 | Knudsen et al. |
| 6,468,961 B1 | 10/2002 | Brodbeck et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,524,305 B1 | 2/2003 | Peterson et al. |
| 6,528,486 B1 | 3/2003 | Larsen et al. |
| 6,544,252 B1 | 4/2003 | Theeuwes et al. |
| 6,593,295 B2 | 7/2003 | Bridon et al. |
| 6,673,767 B1 | 1/2004 | Brodbeck et al. |
| 6,703,359 B1 | 3/2004 | Young et al. |
| 6,706,689 B2 | 3/2004 | Coolidge et al. |
| 6,720,407 B1 | 4/2004 | Hughes et al. |
| 6,767,887 B1 | 7/2004 | Hoffmann et al. |
| 6,821,949 B2 | 11/2004 | Bridon et al. |
| 6,849,708 B1 | 2/2005 | Habener |
| 6,849,714 B1 | 2/2005 | Bridon et al. |

(Continued)

FOREIGN PATENT DOCUMENTS

WO 00/45790 A 8/2000

(Continued)

OTHER PUBLICATIONS

Intarcia Therapeutics: "Intarcia Therapeutics Announces Final Results From A Phase 2 Study Of Injectable Omega Interferon plus Ribavirin for the Treatment of Hepatitis C Genotype-1" NLV Partners Press Coverage Portfolio News, [Online] Apr. 12, 2007, XP002504917.
"Search Report and Written Opinion" dated Dec. 19, 2008 for PCT/US2008/005235, filed Apr. 22, 2008.
Bell, G. I., et al., "Hamster preproglucagon contains the sequence of glucagon and two related peptides," Nature 302:716-718 (1983).
Efendic, S., et al., "Overview of incretin hormones," Horm Metab Res. 36:742-6 (2004).
Eissele, et al., "Rat gastric somatostatin and gastrin release: interactions of exendin-4 and truncated glucagon-like peptide-1 (GLP-1) amide," Life Sci., 55:629-34 (1994).
Eng, J., et al., "Isolation and characterization of exendin-4, an exendin-3 analogue, from Heloderma suspectum venom. Further evidence for an exendin receptor on dispersed acini from guinea pig pancreas," J. Biol. Chem. 267:7402-05 (1992).

(Continued)

*Primary Examiner* — Gyan Chandra
(74) *Attorney, Agent, or Firm* — Gary R. Fabian; Barbara G. McClung (57) ABSTRACT

A suspension formulation of an insulinotropic peptide (e.g., glucagon-like peptide-1 (GLP-1) or exenatide) is described. The suspension formulation comprises (i) a non-aqueous, single-phase vehicle, comprising one or more polymer and one or more one solvent, wherein the vehicle exhibits viscous fluid characteristics, and (ii) a particle formulation comprising the insulinotropic peptide, wherein the peptide is dispersed in the vehicle. The particle formulation further includes a stabilizing component comprising one or more stabilizers, for example, carbohydrates, antioxidants, amino acids, and buffers. Devices for delivering the suspension formulations and methods of use are also described.

16 Claims, 4 Drawing Sheets

U.S. PATENT DOCUMENTS

| | | | |
|---|---|---|---|
| 6,858,576 B1 | 2/2005 | Young et al. |
| 6,872,700 B1 | 3/2005 | Young et al. |
| 6,887,470 B1 | 5/2005 | Bridon et al. |
| 6,887,849 B2 | 5/2005 | Bridon et al. |
| 6,902,744 B1 | 6/2005 | Kolterman et al. |
| 6,903,186 B1 | 6/2005 | Dong |
| 6,924,264 B1 | 8/2005 | Prickett et al. |
| 6,939,556 B2 | 9/2005 | Lautenbach |
| 6,956,026 B2 | 10/2005 | Beeley et al. |
| 6,989,366 B2 | 1/2006 | Beeley et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,843 B2 | 9/2006 | Glaesner et al. |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,199,217 B2 | 4/2007 | DiMarchi et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,297,761 B2 | 11/2007 | Beeley et al. |
| 7,456,254 B2 | 11/2008 | Wright et al. |
| 7,521,423 B2 | 4/2009 | Young et al. |
| 7,563,871 B2 | 7/2009 | Wright et al. |
| 7,612,176 B2 | 11/2009 | Wright et al. |
| 7,682,356 B2 | 3/2010 | Alessi et al. |
| 7,741,269 B2 | 6/2010 | Young et al. |
| 7,879,028 B2 | 2/2011 | Alessi et al. |
| 8,114,437 B2* | 2/2012 | Rohloff et al. | 424/486 |
| 8,206,745 B2* | 6/2012 | Rohloff et al. | 424/486 |
| 2002/0034532 A1 | 3/2002 | Brodbeck et al. |
| 2003/0211974 A1 | 11/2003 | Brodbeck et al. |
| 2004/0002442 A1 | 1/2004 | Pan et al. |
| 2004/0198654 A1 | 10/2004 | Glaesner et al. |
| 2004/0224903 A1 | 11/2004 | Berry et al. |
| 2005/0008661 A1 | 1/2005 | Fereira et al. |
| 2005/0112188 A1* | 5/2005 | Eliaz et al. | 424/450 |
| 2005/0175701 A1 | 8/2005 | Pan et al. |
| 2005/0266087 A1 | 12/2005 | Junnarkar et al. |
| 2005/0276856 A1 | 12/2005 | Fereira et al. |
| 2006/0013879 A9 | 1/2006 | Brodbeck et al. |
| 2006/0084604 A1* | 4/2006 | Kitaura et al. | 514/12 |
| 2006/0141040 A1* | 6/2006 | Chen et al. | 424/486 |
| 2006/0142234 A1 | 6/2006 | Chen et al. |
| 2006/0160736 A1* | 7/2006 | Nadler | 514/12 |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2007/0027105 A1 | 2/2007 | Junnarkar et al. |
| 2007/0281024 A1 | 12/2007 | Lautenbach et al. |
| 2008/0112994 A1 | 5/2008 | Junnarkar et al. |
| 2008/0200383 A1 | 8/2008 | Jennings et al. |
| 2008/0226625 A1 | 9/2008 | Berry et al. |
| 2008/0226689 A1 | 9/2008 | Berry et al. |
| 2009/0087408 A1 | 4/2009 | Berry et al. |
| 2009/0215694 A1 | 8/2009 | Kolterman et al. |
| 2009/0247463 A1 | 10/2009 | Wright et al. |

FOREIGN PATENT DOCUMENTS

| | | |
|---|---|---|
| WO | WO 00/45790 | 8/2000 |
| WO | 2005/048952 A | 6/2005 |
| WO | WO 2005/048952 | 6/2005 |
| WO | 2006/081279 A | 8/2006 |
| WO | 2006/083761 A | 8/2006 |
| WO | WO 2006/081279 | 8/2006 |
| WO | WO 2006/083761 | 8/2006 |
| WO | 2006/101815 A | 9/2006 |
| WO | WO 2006/101815 | 9/2006 |
| WO | 2007/075534 A | 7/2007 |
| WO | 2007/084460 A | 7/2007 |
| WO | WO 2007/075534 | 7/2007 |
| WO | WO 2007/084460 | 7/2007 |
| WO | 2008/021133 A | 2/2008 |
| WO | WO 2008/021133 | 2/2008 |
| WO | 2008/061355 A | 5/2008 |
| WO | WO 2008/061355 | 5/2008 |

OTHER PUBLICATIONS

Eng, J., et al., "Purification and structure of exendin-3, a new pancreatic secretagogue isolated from Heloderma horridum venom," J. Biol. Chem., 265:20259-62 (1990).

Ghiglione, M., et al., "How glucagon-like is glucagon-like peptide-1?" Diabetologia, 27:599-600 (1984).

Göke R, et al., "Exendin-4 is a high potency agonist and truncated exendin-(9-39)-amide an antagonist at the glucagon-like peptide 1-(7-36)-amide receptor of insulin-secreting beta-cells," J Biol Chem. 268:19650-55 (1993).

Gutniak M., et al., "Antidiabetogenic effect of glucagon-like peptide-1 (7-36)amide in normal subjects and patients with diabetes mellitus," N Engl J Med. May 14;326(20):1316-22 (1992).

Heinrich, G., et al., "Pre-proglucagon messenger ribonucleic acid: nucleotide and encoded amino acid sequences of the rat pancreatic complementary deoxyribonucleic acid," Endocrinol., 115:2176-2181 (1984).

Lopez, et al., "Mammalian pancreatic preproglucagon contains three glucagon-related peptides," Proc. Natl. Acad. Sci. U.S.A. 80:5485-5489 (1983).

Lund, et al., "Pancreatic preproglucagon cDNA contains two glucagon-related coding sequences arranged in tandem," Proc. Natl. Acad. Sci. U.S.A. 79:345-349 (1982).

Mojsov, S., "Structural requirements for biological activity of glucagon-like peptide-I," Int. J. Peptide Protein Research, 40:333-343 (1992).

Nauck, M.A., et al., "Normalization of fasting glycaemia by intravenous GLP-1 ([7-36 amide] or [7-37]) in type 2 diabetic patients," Diabet. Med. 15(11):937-45(1998).

Patzelt, C., et al., "Identification and processing of proglucagon in pancreatic islets," Nature, 282:260-266 (1979).

Pohl, M., et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273:9778-84 (1998).

Schepp, et al., "Exendin-4 and exendin-(9-39)NH2: agonist and antagonist, respectively, at the rat parietal cell receptor for glucagon-like peptide-1-(7-36)NH2," Eur. J. Pharmacol., 269:183-91 (1994).

Tseng, C., et al., "Glucose-dependent insulinotropic peptide: structure of the precursor and tissue-specific expression in rat," PNAS 90:1992-1996 (1993).

Young, A.A., et al., "Glucose-lowering and insulin-sensitizing actions of exendin-4: studies in obese diabetic (ob/ob, db/db) mice, diabetic fatty Zucker rats, and diabetic rhesus monkeys (Macaca mulatta)," Diabetes 48(5):1026-34 (1999).

"Intarcia Therapeutics Announces Final Results from a Phase 2 Study of Injectable Omega Interferon plus Ribavirin for the Treatment of Hepatits C Genotype-1," NLV Partners Press Coverage Portofolio News, Apr. 12, 2007.

PCT International Preliminary Report on Patentability, Application No. PCT/US2008/005235, Apr. 22, 2008, which corresponds to U.S. Appl. No. 12/148,896.

PCT Written Opinion of the International Searching Authority (PCT Rule 43bis.1), International Application No. PCT/US2008/005235, Apr. 22, 2008, which corresponds to U.S. Appl. No. 12/148,896.

Press Release, Intarcia Therapeutics, Inc., "Intarcia Presents Positive ITCA 650 Phase 2 Study Results for Type 2 Diabetes at EASD," Sep. 22, 2010.

"Comparing ITCA 650, continuous subcutaneous delivery of exenatide via DUROS® device, vs. twice daily exenatide injections in metformin-treated type 2 diabetes," ITCA 650 phase 2 oral presentation at the 46th Annual Meeting of the European Association for the Study of Diabetes in Stockholm, Sweden; Sep. 20-24, 2010.

* cited by examiner

His-Ala-Glu-Gly-Thr-Phe-Thr-Ser-Asp-Val-
Ser-Ser-Tyr-Leu-Glu-Gly-Gln-Ala-Ala-Lys-
Glu-Phe-Ile-Ala-Trp-Leu-Val-Lys-Gly-Arg-NH$_2$

Figure 1A

His-Gly-Glu-Gly-Thr-Phe-Thr-Ser-Asp-Leu-
Ser-Lys-Gln-Met-Glu-Glu-Glu-Ala-Val-Arg-
Leu-Phe-Ile-Glu-Trp-Leu-Lys-Asn-Gly-Gly-
Pro-Ser-Ser-Gly-Ala-Pro-Pro-Pro-Ser-NH$_2$

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

SUSPENSION FORMULATIONS OF INSULINOTROPIC PEPTIDES AND USES THEREOF

CROSS-REFERENCE TO RELATED APPLICATIONS

This application claims the benefit of U.S. Provisional Application Ser. No. 60/926,005, filed 23 Apr. 2007, and U.S. Provisional Application Ser. No. 61/072,202, filed 28 Mar. 2008, which applications are herein incorporated by reference in their entireties; and is a continuation-in-part of U.S. patent application Ser. No. 11/347,562, filed 3 Feb. 2006, now U.S. Pat. No. 8,114,437, which claims the benefit of U.S. Provisional Application Ser. No. 60/650,225, filed 3 Feb. 2005.

TECHNICAL FIELD

The present invention relates to organic chemistry, formulation chemistry, and peptide chemistry applied to pharmaceutical research and development. Aspects of the present invention provide suspension formulations of insulinotropic peptides for use in mammals and for the treatment of diseases or conditions.

BACKGROUND OF THE INVENTION

Glucagon-like peptide-1 (GLP-1) is an important hormone and a fragment of the human proglucagon molecule. GLP-1 is rapidly metabolized by a peptidase (dipeptidylpeptidase IV or DPP-IV). A fragment of GLP-1, glucagon-like peptide-1 (7-36) amide (glucagon-like insulinotropic peptide, or GLIP) is a gastrointestinal peptide that potentiates the release of insulin in physiologic concentrations (Gutniak M., et al., N Engl J. Med. 1992 May 14; 326(20):1316-22). GLP-1 and GLP-1(7-36) amide are incretins. Incretins are gastrointestinal hormones that cause an increase in the amount of insulin released from beta cells after eating.

Food intake, as well as stimulation of the sympathetic nervous system, stimulates secretion of GLP-1 in the small intestine of mammals. Further, GLP-1 stimulates the production and secretion of insulin, the release of somatostatin, glucose utilization by increasing insulin sensitivity, and, in animal studies, also stimulates beta-cell function and proliferation.

GLP-1(7-36) amide and GLP-1(7-37) normalize fasting hyperglycemia in Type 2 diabetic patients (Nauck, M. A., et al., Diabet. Med. 15(11):937-45 (1998)).

Exendin-4 is an incretin mimetic (i.e., it mimics physiological effects of incretins) purified from *Heloderma suspectum* venom (Eng, J., et al., J. Biol. Chem. 267:7402-05 (1992)) and shows structural relationship to the incretin hormone GLP-1(7-36) amide. Exendin-4 and truncated exendin-(9-39) amide specifically interact with the GLP-1 receptor on insulinoma-derived cells and on lung membranes (Göke R, et al., J. Biol. Chem. 268:19650-55 (1993)). Exendin-4 has approximately 53% homology to human GLP-1 (Pohl, M., et al., J Biol. Chem. 273:9778-84 (1998)). Unlike GLP-1, however, exendin-4 is resistant to degradation by DPP-IV. A glycine substitution confers resistance to degradation by DPP-IV (Young, A. A., et al., Diabetes 48(5):1026-34 (1999)).

SUMMARY OF THE INVENTION

The present invention relates to suspension formulations comprising a particle formulation and a suspension vehicle, as well as devices comprising such formulations, methods of making such formulations and devices, and methods of use thereof.

In one aspect, the present invention relates to a suspension formulation comprising, a particle formulation comprising an insulinotropic peptide and one or more stabilizer selected from the group consisting of carbohydrates, antioxidants, amino acids, buffers, and inorganic compounds. The suspension formulation further comprises a non-aqueous, single-phase suspension vehicle comprising one or more polymer and one or more solvent. The suspension vehicle exhibits viscous fluid characteristics and the particle formulation is dispersed in the vehicle.

In one embodiment, the suspension formulation comprises a particle formulation comprising an insulinotropic peptide, a disaccharide (e.g., sucrose), methionine, and a buffer (e.g., citrate), and a non-aqueous, single-phase suspension vehicle comprising one or more pyrrolidone polymer (e.g., polyvinylpyrollidone) and one or more solvent (e.g., lauryl lactate, lauryl alcohol, benzyl benzoate, or mixtures thereof.

Examples of insulinotropic peptides include, but are not limited to, glucagon-like peptide-1 (GLP-1), exenatide, and derivatives or analogues thereof. In one embodiment of the invention, the insulinotropic peptide is GLP-1(7-36) amide. In another embodiment of the invention, the insulinotropic peptide is exenatide.

The particle formulations of the present invention may further comprise a buffer, for example, selected from the group consisting of citrate, histidine, succinate, and mixtures thereof.

The particle formulations of the present invention may further comprise an inorganic compound, for example, selected from the group consisting of citrate, histidine, succinate, and mixtures thereof. NaCl, $Na_2SO_4$, $NaHCO_3$, KCl, $KH_2PO_4$, $CaCl_2$, and $MgCl_2$.

The one or more stabilizer in the particle formulations may comprise, for example, a carbohydrate selected from the group consisting of lactose, sucrose, trehalose, mannitol, cellobiose, and mixtures thereof.

The one or more stabilizer in the particle formulations may comprise, for example, a antioxidant selected from the group consisting of methionine, ascorbic acid, sodium thiosulfate, ethylenediaminetetraacetic acid (EDTA), citric acid, cysteines, thioglycerol, thioglycolic acid, thiosorbitol, butylated hydroxanisol, butylated hydroxytoluene, and propyl gallate, and mixtures thereof.

The one or more stabilizer in the particle formulations may comprise an amino acid.

In one embodiment, the solvent of the suspension vehicle of the present invention is selected from the group consisting of lauryl lactate, lauryl alcohol, benzyl benzoate, and mixtures thereof. An example of a polymer that can be to formulate the suspension vehicle is a pyrrolidone (e.g., polyvinylpyrrolidone). In a preferred embodiment, the polymer is a pyrrolidone and the solvent is benzyl benzoate.

The suspension formulation typically has an overall moisture content less than about 10 wt % and in a preferred embodiment less than about 5 wt %.

An implantable drug delivery device may be used to contain and deliver the suspension formulation of the present invention. In one embodiment the device is an osmotic delivery device.

The suspension formulations of the present invention can be used to treat any of a number of disease states or conditions in a subject in need of treatment, for example, type II diabetes. In one embodiment, an implantable drug delivery device delivers a suspension formulation of the present invention at a substantially uniform rate for a period of about one month to about a year. The device may, for example, be implanted subcutaneously in a convenient location.

The present invention also includes methods of manufacturing the suspension formulations, particle formulations, suspension vehicles, and devices of the present invention as described herein.

These and other embodiments of the present invention will readily occur to those of ordinary skill in the art in view of the disclosure herein.

BRIEF DESCRIPTION OF THE FIGURES

FIGS. 1A and 1B presents the sequences of two examples of insulinotropic peptides: FIG. 1A, glucagon-like peptide 1 (7-36) amide (GLP-1(7-36) amide) (SEQ ID NO:1), and FIG. 1B, synthetic exenatide peptide (SEQ ID NO:2).

DETAILED DESCRIPTION OF THE INVENTION

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, mixtures of peptides, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogues, and/or amino acid mimetic). Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl).

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotropic" as used herein refers to the ability of a compound, e.g., a peptide, to stimulate or affect the production and/or activity of insulin (e.g., an insulinotropic hormone). Such compounds typically stimulate the secretion or biosynthesis of insulin in a subject.

The phrase "insulinotropic peptide" as used herein includes, but is not limited to, glucagon-like peptide 1 (GLP-1), as well as derivatives and analogues thereof, and exenatide, as well as derivatives and analogues thereof.

The term "vehicle" as used herein refers to a medium used to carry a compound. Vehicles of the present invention typically comprise components such as polymers and solvents. The suspension vehicles of the present invention typically comprise solvents and polymers that are used to prepare suspension formulations of polypeptide particles.

The phrase "phase separation" as used herein refers to the formation of multiple phases (e.g., liquid or gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a peptide, in a suspension vehicle.

The phrase "chemically stable" as used herein refers to formation in a formulation of an acceptable percentage of degradation products produced over a defined period of time by chemical pathways, such as deamidation, (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where F/A=shear stress (force per unit area),
μ=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include, measurement of a kinematic viscosity using a viscometers, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, preferably less than or equal to about 5 wt %, and more preferably less than about 4 wt %.

The term "subject" as used herein refers to any member of the subphylum *chordata*, including, without limitation, humans and other primates, including non-human primates such as rhesus macaque, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The terms "drug," "therapeutic agent", and "beneficial agent" are used interchangeably to refer to any therapeutically active substance that is delivered to a subject to produce a desired beneficial effect. In one embodiment of the present invention, the drug is an insulinotropic peptide, e.g., GLP-1, exenatide, and derivatives or analogues thereof. The devices and methods of the present invention are well suited for the delivery of polypeptides as well as small molecules and combinations thereof.

The term "osmotic delivery device" as used herein typically refers to a device used for delivery of one or more beneficial agent (e.g., an insulinotropic peptide) to a subject, wherein the device comprises, for example, a reservoir (made, for example, from a titanium alloy) having a lumen that contains a suspension formulation (e.g., comprising an insulinotropic peptide) and an osmotic agent formulation. A piston assembly positioned in the lumen isolates the suspension formulation from the osmotic agent formulation. A semipermeable membrane positioned at a first distal end of the reservoir adjacent the osmotic agent formulation, as well as a flow modulator (which defines a delivery orifice through which the suspension formulation exits the device) that is positioned at a second distal end of the reservoir adjacent the suspension formulation. Typically, the osmotic delivery device is implanted within the subject, for example, subcutaneously (e.g., in the inside, outside, or back of the upper arm; or in the abdominal area).

2.0.0 General Overview of the Invention

Before describing the present invention in detail, it is to be understood that this invention is not limited to particular types of drug delivery, particular types of drug delivery devices, particular sources of peptides, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In one aspect, the present invention relates to a suspension formulation, comprising a particle formulation and a suspension vehicle. The particle formulation includes, but is not limited to, an insulinotropic peptide and one or more stabilizer. The one or more stabilizer is typically selected from the group consisting of carbohydrates, antioxidants, amino acids, and buffers. The suspension vehicle is typically a non-aqueous, single-phase suspension vehicle comprising one or more polymer and one or more solvent. The suspension vehicle exhibits viscous fluid characteristics. The particle formulation is uniformly dispersed in the vehicle.

In one embodiment of the present invention the insulinotropic peptide is a glucagon-like peptide-1 (GLP-1), a derivative of GLP-1 (e.g., GLP-1(7-36) amide), or an analogue of GLP-1.

In another embodiment of the present invention insulinotropic peptide is exenatide, a derivative of exenatide, or an analogue of exenatide.

The particle formulation of the present invention typically includes one or more of the following stabilizers: one or more carbohydrate (e.g., a disaccharide, such as, lactose, sucrose, trehalose, cellobiose, and mixtures thereof); one or more antioxidant (e.g., methionine, ascorbic acid, sodium thiosulfate, ethylenediaminetetraacetic acid (EDTA), citric acid, butylated hydroxytoluene, and mixtures thereof); and one or more buffer (e.g., citrate, histidine, succinate, and mixtures thereof). In a preferred embodiment, the particle formulation comprises an insulinotropic peptide, sucrose, methionine, and citrate buffer. The ratio of insulinotropic peptide to sucrose+methionine is typically about 1/20, about 1/10, about 1/5, about 1/2, about 5/1, about 10/1, or about 20/1, preferably between about 1/5 to 5/1, more preferably between about 1/3 to 3/1. The particle formulation is preferably a particle formulation prepared by spray drying and has a low moisture content, preferably less than or equal to about 10 wt %, more preferably less or equal to about 5 wt %. In another embodiment the particle formulation can be lyophilized.

The suspension vehicle of the present invention comprises one or more solvent and one or more polymer. Preferably the solvent is selected from the group consisting of lauryl lactate, lauryl alcohol, benzyl benzoate, and mixtures thereof. More preferably the solvent is lauryl lactate or benzyl benzoate. Preferably the polymer is a pyrrolidone. In some embodiments the polymer is polyvinylpyrrolidone (e.g., polyvinylpyrrolidone K-17, which typically has an approximate average molecular weight range of 7,900-10,800). In one embodiment of the present invention the solvent consists essentially of benzyl benzoate and polyvinylpyrrolidone.

The suspension formulation typically has a low overall moisture content, for example, less than or equal to about 10 wt % and in a preferred embodiment less than or equal to about 5 wt %.

In another aspect, the present invention relates to an implantable drug delivery device, comprising a suspension formulation of the present invention. In a preferred embodiment, the drug delivery device is an osmotic delivery device.

The present invention further includes methods of manufacturing the suspension formulations of the present invention, as well as osmotic delivery devices loaded with a suspension formulation of the present invention. In one embodiment, the present invention includes a method of manufacturing an osmotic delivery device comprising, loading a suspension formulation into a reservoir of the osmotic delivery device.

In another aspect, the present invention relates to a method of treating diabetes (e.g., diabetes mellitus type 2 or gestational diabetes) in a subject in need of such treatment, comprising delivering a suspension formulation of the present invention from an osmotic delivery device at a substantially uniform rate. Typically the suspension formulation is delivered for a period of about one month to about a year, preferably about three months to about a year. The method may further include subcutaneously inserting an osmotic delivery device, loaded with a suspension formulation of the present invention, into the subject. In further aspects, the present invention relates to methods of stimulating insulin secretion, suppressing glucagon secretion, slowing gastric emptying, treating diabetic related disorders, treating hyperglycemia, treating obesity, controlling appetite, reducing weight, and regulating gastrointestinal motility.

2.1.0 Formulations and Compositions 2.1.1 Particle Formulations

In one aspect, the present invention provides a pharmaceutical composition comprising a suspension formulation of an insulinotropic peptide, for example, GLP-1 or exenatide. The suspension formulation comprises a non-aqueous, single-phase vehicle including at least one polymer and at least one solvent. The vehicle preferably exhibits viscous fluid characteristics. The peptide component comprises the insulinotropic peptide in a particle formulation that is dispersed in the vehicle. Typically, the particle formulation includes a stabilizing component comprising one of more stabilizer component selected from the group consisting of carbohydrates, antioxidants, amino acids, buffers, and inorganic compounds.

Insulinotropic peptides useful in the practice of the present invention include, but are not limited to, GLP-1 and exenatide.

Bell, G. I., et al., (Nature 302:716-718 (1983)) discovered that proglucagon (Lund, et al., Proc. Natl. Acad. Sci. U.S.A. 79:345-349 (1982); Patzelt, et al., Nature, 282:260-266 (1979)) contained three discrete, highly homologous peptide regions which were designated glucagon, glucagon-like peptide 1 (GLP-1), and glucagon-like peptide 2 (GLP-2). Lopez, et al., (Proc. Natl. Acad. Sci. U.S.A. 80:5485-5489 (1983)) demonstrated that the peptide sequence of GLP-1 was a sequence of 37 amino acids and that the peptide sequence of GLP-2 was a sequence of 34 amino acids.

Studies of the structure of rat preproglucagon revealed a similar pattern of proteolytic cleavage resulting in the formation of glucagon, GLP-1, and GLP-2 (Heinrich, G., et al., Endocrinol., 115:2176-2181 (1984)). Human, rat, bovine, and hamster sequences of GLP-1 were found to be identical (Ghiglione, M., et al., Diabetologia, 27:599-600 (1984)).

Figure 1A:
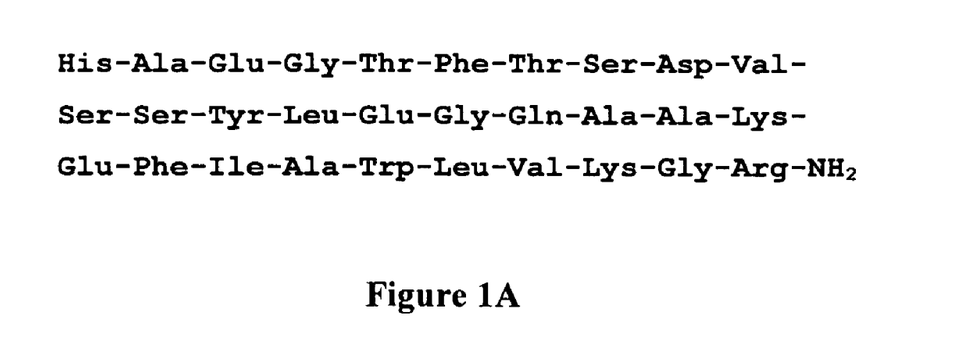
Figure 1B:
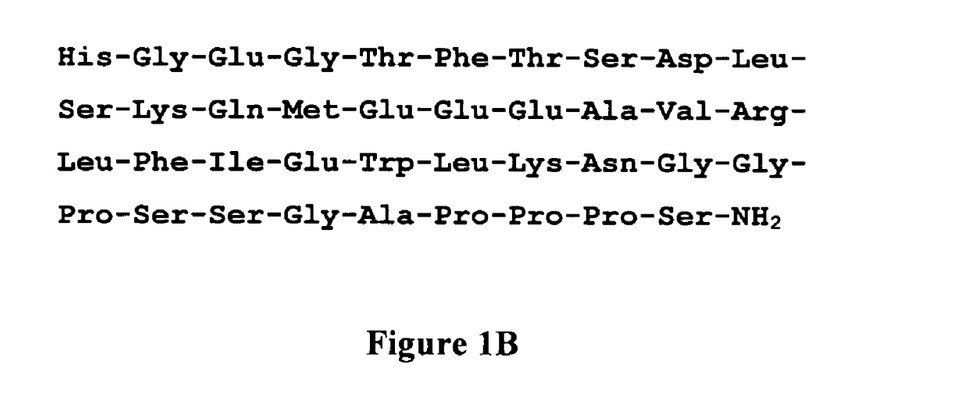

Cleavage of preproglucagon first yields GLP-1(1-37), a 37 amino acid peptide that has poor insulinotropic activity. A subsequent cleavage of the peptide bond between amino acid residues 6 and 7 produces a biologically active GLP-1 referred to as GLP-1(7-37) (by convention the amino terminus of GLP-1(7-37) was assigned number 7 and the carboxy terminus number 37). Approximately 80% of GLP-1(7-37) that is produced in mammals is amidated at the C-terminus after removal of the terminal glycine residue in L-cells, resulting in GLP-1(7-36) amide. The biological effects and metabolic turnover of the free acid GLP-1(7-37), and the amide, GLP-1(7-36) amide, are essentially the same. The sequence of GLP-1(7-36) amide is presented in FIG. 1A.

GLP-1 (including three forms of the peptide, GLP-1(1-37), GLP-1(7-37) and GLP-1(7-36) amide, as well as analogs of GLP-1) have been shown to stimulate insulin secretion (i.e., it is insulinotropic) which induces glucose uptake by cells and results in decreases in serum glucose levels (see, e.g., Mojsov, S., Int. J. Peptide Protein Research, 40:333-343 (1992)). Another GLP-1 analogue is liraglutide, which is a long-acting DPP-4-resistant GLP-1 receptor agonist. Liraglutide has 97% identity to GLP-1(7-37). Liraglutide is also called N,N-2211 and [Arg34, Lys26]-(N-epsilon-(gamma-Glu(N-alpha-hexadecanoyl))-GLP-1(7-37) (see, e.g., U.S. Pat. No. 6,969,702).

Numerous GLP-1 derivatives and analogues demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217). Accordingly, for ease of discussion herein, the family of GLP-1 derivatives and analogues having insulinotropic activity is referred to collectively as GLP-1.

Gastric inhibitory peptide (GIP) is also an insulinotropic peptide (Efendic, S., et al., Horm Metab Res. 36:742-6 (2004)). GIP is a hormone secreted by the mucosa of the duodenum and jejunum in response to absorbed fat and carbohydrate that stimulate the pancreas to secrete insulin. GIP is also known as glucose-dependent insulinotropic polypeptide. GIP is a 42-amino acid gastrointestinal regulatory peptide that stimulates insulin secretion from pancreatic beta cells in the presence of glucose (Tseng, C., et al., PNAS 90:1992-1996 (1993)).

The exendins are peptides that were isolated from the venom of the Gila-monster. Exendin-4 is present in the venom of *Heloderma suspectum* (Eng, J., et al., J. Biol. Chem., 265:20259-62 (1990); Eng., J., et al., J. Biol. Chem., 267:7402-05 (1992); U.S. Pat. No. 5,424,286). The exendins have some sequence similarity to several members of the glucagon-like peptide family, with the highest homology, 53%, being to GLP-1(7-36) amide (Goke, et al., J. Biol. Chem., 268:19650-55 (1993)).

Exendin-4 acts at GLP-1 receptors on insulin-secreting beta-TC1 cells, dispersed acinar cells from guinea pig pancreas, and parietal cells from stomach. The exendin-4 peptide also stimulates somatostatin release and inhibits gastrin release in isolated stomachs (Goke, et al., J. Biol. Chem. 268:19650-55 (1993); Schepp, et al., Eur. J. Pharmacol., 69:183-91 (1994); Eissele, et al., Life Sci., 55:629-34 (1994)). Based on their insulinotropic activities, use of exendin-3 and exendin-4 for the treatment of diabetes mellitus and the prevention of hyperglycemia has been proposed (U.S. Pat. No. 5,424,286).

Numerous exendin-4 derivatives and analogues (including, e.g., exendin-4 agonists) demonstrating insulinotropic action are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). Exenatide is a synthetic peptide having the same 39 amino acid sequence as exendin-4. Exenatide is a peptide incretin mimetic that exhibits glucoregulatory activities similar to the mammalian incretin hormone glucagon-like peptide 1 (GLP-1). Incretin hormones are hormones that cause an increase in the amount of insulin released when glucose levels are normal or particularly when they are elevated. Incretin hormones affect other activities defined by insulin secretion, for example, they can reduce glucagon production and delay gastric emptying. Further, incretin hormones may improve insulin sensitivity and possibly increase islet cell neogenesis.

For ease of discussion herein, the family of exendin-4 peptides, including synthetic versions (e.g., exenatide), derivatives and analogues having insulinotropic activity, is referred to collectively as exenatide.

In one aspect, the present invention provides particle formulations of insulinotropic peptides that can be used to prepare suspension formulations. The insulinotropic peptides of the present invention shall not be limited by method of synthesis or manufacture and shall include those obtained from natural sources, or synthesized or manufactured by recombinant (whether produced from cDNA or genomic DNA), synthetic, transgenic, and gene-activated methods. In preferred embodiments of the present invention the insulinotropic peptide is a GLP-1 peptide or an exendin peptide (as described herein above), for example, GLP-1(7-36) amide or exenatide. The present invention also includes combinations of two or more insulinotropic peptides, for example, GLP-1(7-36) amide and GIP.

Particle formulations of the invention are preferably chemically and physically stable for at least 1 month, preferably at least 3 months, more preferably at least 6 months, more preferably at least 12 months at delivery temperature. The delivery temperature is typically normal human body temperature, for example, about 37° C., or slightly higher, for example, about 40° C. Further, particle formulations of the present invention are preferably chemically and physically stable for at least 3 months, preferably at least 6 months, more preferably at least 12 months, at storage temperature. Examples of storage temperatures include refrigeration temperature, for example, about 5° C., or room temperature, for example, about 25° C.

A particle formulation may be considered chemically stable if less than about 25%, preferably less than about 20%, more preferably less than about 15%, more preferably less than about 10%, and more preferably less than about 5% breakdown products of the peptide particles are formed after about 3 months, preferably after about 6 months, preferably after about 12 months at delivery temperature and after about 6 months, after about 12 months, and preferably after about 24 months at storage temperature.

A particle formulation may be considered physically stable if less than about 10%, preferably less than about 5%, more preferably less than about 3%, more preferably less than 1% aggregates of the peptide particles are formed after about 3 months, preferably after about 6 months, at delivery temperature and about 6 months, preferably about 12 months, at storage temperature.

To preserve protein stability generally an insulinotropic peptide solution is kept in a frozen condition and lyophilized or spray dried to a solid state. Tg (glass transition temperature) may be one factor to consider in achieving stable compositions of peptide. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. No mobility of molecules correlates with no instability issues. Tg is also dependent on the moisture level in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. The particles are preferably substantially uniform in shape and size.

A typical spray dry process may include, for example, loading a spray solution containing a peptide, for example, an insulinotropic peptide (e.g., GLP-1(7-36) amide or exenatide), and stabilizing excipients into a sample chamber. The sample chamber is typically maintained at a desired temperature, for example, refrigeration to room temperature. Refrigeration generally promotes stability of the protein. A solution, emulsion, or suspension is introduced to the spray dryer where the fluid is atomized into droplets. Droplets can be formed by use of a rotary atomizer, pressure nozzle, pneumatic nozzle, or sonic nozzle. The mist of droplets is immediately brought into contact with a drying gas in a drying chamber. The drying gas removes solvent from the droplets and carries the particles into a collection chamber. In spray drying, factors that can affect yield include, but are not limited to, localized charges on particles (which may promote adhesion of the particles to the spray dryer) and aerodynamics of the particles (which may make it difficult to collect the particles). In general, yield of the spray dry process depends in part on the particle formulation.

In one embodiment of the present invention, the particles are sized such that they can be delivered via an implantable drug delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, preferably is less than about 20%, more preferably is less than about than 10%, of the diameter of the delivery orifice. In an embodiment of the particle formulation for use with an osmotic delivery system, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns. In one embodiment, the orifice is about 0.25 mm (250 µm) and the particle size is approximately 3-5 µm.

In a preferred embodiment, when the particles are incorporated in a suspension vehicle they do not settle in less than about 3 months at delivery temperature. Generally speaking, smaller particles tend to have a lower settling rate in viscous suspension vehicles than larger particles. Accordingly, micron- to nano-sized particles are typically desirable. In an embodiment of the particle formulation of the present invention for use in an implantable osmotic delivery device, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns.

In one embodiment, a particle formulation of the present invention comprises one or more insulinotropic peptide, as described above, one or more stabilizers, and optionally a buffer. The stabilizers may be, for example, carbohydrate, antioxidant, amino acid, buffer, or inorganic compound. The amounts of stabilizers and buffer in the particle formulation can be determined experimentally based on the activities of the stabilizers and buffers and the desired characteristics of the formulation. Typically, the amount of carbohydrate in the formulation is determined by aggregation concerns. In general, the carbohydrate level should not be too high so as to avoid promoting crystal growth in the presence of water due to excess carbohydrate unbound to insulinotropic peptide. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize insulinotropic peptide during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteines, thioglycerol, thioglycolic acid, thiosorbitol, butylated hydroxanisol, butylated hydroxytoluene, and propyl gallate.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, trytophan, serine, asparagines, cysteine, tyrosine, lysine, and norleucine. Preferred amino acids include those that readily oxidize, e.g., cysteine, methionine, and trytophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, $Na_2SO4$, $NaHCO_3$, KCl, $KH_2PO4$, $CaCl_2$, and $MgCl_2$.

In addition, the particle formulation may include other excipients, such as surfactants, bulking agents, and salts. Examples of surfactants include, but are not limited to, Polysorbate 20, Polysorbate 80, PLURONIC® (BASF Corporation, Mount Olive, N.J.) F68, and sodium docecyl sulfate (SDS). Examples of bulking agents include, but are not limited to, mannitol and glycine. Examples of salts include, but are not limited to, sodium chloride, calcium chloride, and magnesium chloride.

All components included in the particle formulation are typically acceptable for pharmaceutical use in mammals, in particular, in humans.

Table 1 below presents examples of particle formulation composition ranges for particles comprising exenatide.

TABLE 1

|  | Range (% by weight) | Preferred Range (% by weight) | More Preferred Range (% by weight) |
| --- | --- | --- | --- |
| Particle loading in suspension formulation In Particles | 0.1 to 99.9% | 1 to 50% | 5 to 40% |
| Exenatide peptide | 1 to 99% | 5 to 70% | 10 to 60% |
| Carbohydrate | 0 to 99% | 2.5 to 40% | 5 to 30% |
| Antioxidant and/or amino acid | 0 to 99% | 2.5 to 30% | 5 to 30% |
| Buffer | 0 to 99% | 10 to 80% | 10 to 70% |

In one embodiment, the exenatide particle formulation comprises exenatide peptide, sucrose (carbohydrate), methionine (antioxidant), and sodium citrate/citric acid (citrate buffer).

Table 2 below presents examples of particle formulation composition ranges for particles comprising GLP-1.

TABLE 2

|  | Range (% by weight) | Preferred Range (% by weight) | More Preferred Range (% by weight) |
| --- | --- | --- | --- |
| Particle loading in suspension formulation In Particles | 0.1 to 99.9% | 1 to 50% | 10-50% |
| GLP-1 peptide | 1 to 99% | 5 to 95% | 30-90% |
| Carbohydrate and/or Antioxidant and/or amino acid | 0 to 99% | 0.1 to 30% | 2-20% |
| Buffer | 0 to 99% | 0.1 to 50% | 2-30% |

Within these weight percent ranges for components of the particle formulation, some preferred component ratios are as follows: insulinotropic peptide (e.g., exenatide or GLP-1) to antioxidant (e.g., methionine)—1/10, 1/5, 1/2.5, 1/1, 2.5/1, 5/1, 10/1, preferably between about 1/5 to 5/1, more preferably between about 1/3 to 3/1 (these same component ratios apply to insulinotropic peptide to amino acid ratios); insulinotropic peptide (e.g., exenatide or GLP-1) to carbohydrate (e.g., sucrose)—1/10, 1/5, 1/2.5, 1/1, 2.5/1, 5/1, 10/1, preferably between about 1/5 to 5/1, more preferably between about 1/3 to 3/1; and/or insulinotropic peptide (e.g., exenatide or GLP-1) to antioxidant+carbohydrate (e.g., methionine+sucrose)—1/20, 1/10, 1/5, 1/2, 5/1, 10/1, 20/1, preferably between about 1/5 to 5/1, more preferably between about 1/3 to 3/1 (these same component ratios apply to insulinotropic peptide to amino acid+carbohydrate ratios). The present invention also includes ranges corresponding to all of these ratios, for example, between about 1/20 and about 20/1, between about 1/10 and about 10/1, between about 1/5 and about 5/1, and so on, as well as, for example, between about 1/5 and about 3/1, and so on.

In summary, insulinotropic peptides are formulated into dried powders in solid state, which preserve maximum chemical and biological stability of proteins or peptides. The particle formulation offers long term storage stability at high temperature, and therefore, allows delivery to a subject of stable and biologically effective peptide for extended periods of time.

Particle size distribution of the dry particle powder can be well controlled (0.1 micron—20 micron), for example, by using the methods of spray drying or lyophilization to prepare the particle formulations. The process parameters for formation of the dry powder are optimal to produce particles with desired particle size distribution, density, and surface area.

The selected excipients and buffer in the particle formulation may provide, for example, the following functions: density modification of the dry powder; preservation of the peptide chemical stability; maintenance of the peptide's physical stability (e.g., high glass transition temperature, and avoiding phase to phase transition); producing homogenous dispersions in suspension by use of bulking agents; modification of hydrophobicity and/or hydrophilicity to manipulate dry powder solubility in selected solvents; and, manipulation of pH during processing and maintenance of pH in the product (for solubility and stability).

The particle formulations of the present invention are exemplified herein below with reference to exenatide and GLP-1(7-36) amide as exemplary insulinotropic peptides (see, Example 1 and Example 2). These examples are not intended to be limiting.

2.1.2 Vehicle and Suspension Formulations

In one aspect of the present invention, the suspension vehicle provides a stable environment in which the insulinotropic peptide particle formulation is dispersed. The particle formulations are chemically and physically stable (as described above) in the suspension vehicle. The suspension vehicle typically comprises one or more polymer and one or more solvent that form a solution of sufficient viscosity to uniformly suspend the particles comprising the insulinotropic peptide.

The viscosity of the suspension vehicle is typically sufficient to prevent the particle formulation from settling during storage and use in a method of delivery, for example, in an implantable, drug delivery device. The suspension vehicle is biodegradable in that the suspension vehicle disintegrates or breaks down over a period of time in response to a biological environment. The disintegration of the suspension vehicle may occur by one or more physical or chemical degradative processes, such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the patient.

The solvent in which the polymer is dissolved may affect characteristics of the suspension formulation, such as the behavior of the insulinotropic peptide particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. However, typically the insulinotropic peptide is substantially insoluble in the solvent. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and combinations thereof.

Examples of polymers for formulation of the suspension vehicles of the present invention include, but are not limited to, a polyester (e.g., polylactic acid or polylacticpolyglycolic acid), pyrrolidone (e.g., polyvinylpyrrolidone (PVP) having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. In one embodiment, the polymer is PVP having a molecular weight of 2,000 to 1,000,000. In a preferred embodiment the polymer is polyvinylpyrrolidone K-17 (typically having an approximate average molecular weight range of 7,900-10,800). Polyvinylpyrrolidone can be characterized by its K-value (e.g., K-17), which is a viscosity index. The polymer used in the suspension vehicle may include one or more different polymers or may include different grades of a single polymer. The polymer used in the suspension vehicle may also be dry or have a low moisture content.

Generally speaking, a suspension vehicle according to the present invention may vary in composition based on the desired performance characteristics. In one embodiment, the suspension vehicle may comprise about 40% to about 80% (w/w) polymer(s) and about 20% to about 60% (w/w) solvent(s). Preferred embodiments of a suspension vehicle include vehicles formed of polymer(s) and solvent(s) combined at the following ratios: about 25% solvent and about 75% polymer; about 50% solvent and about 50% polymer; about 75% solvent and about 25% polymer.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the insulinotropic peptide at a desired rate. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. The viscosity may be measured at 37° C., at a shear rate of $10^{-4}$/sec, using a parallel plate rheometer. In some embodiments, the viscosity of the suspension vehicle ranges from approximately 5,000 poise to approximately 50,000 poise. In preferred embodiments, the viscosity range is between about 12,000 to about 18,000 poise at 33° C.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The particle formulation, comprising an insulinotropic peptide, is added to the suspension vehicle to form a suspension formulation. The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

The suspension formulations of the present invention are exemplified herein below with reference to exenatide and GLP-1(7-36) amide as exemplary insulinotropic peptides (see, Example 3 and Example 4). These examples are not intended to be limiting.

In summary, the components of the suspension vehicle provide biocompatibility. Components of the suspension vehicle offer suitable chemico-physical properties to form stable suspensions of, for example, dry powder particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

3.0.0 Delivery of Suspension Formulations

The suspension formulations described herein may be used in an implantable, drug delivery device to provide sustained delivery of a compound over an extended period of time, such as over weeks, months, or up to about one year. Such an implantable drug delivery device is typically capable of delivering the compound at a desired flow rate over a desired period of time. The suspension formulation may be loaded into the implantable, drug delivery device by conventional techniques.

The suspension formulation may be delivered, for example, using an osmotically, mechanically, electromechanically, or chemically driven drug delivery device. The insulinotropic peptide is delivered at a flow rate that is therapeutically effective to the subject in need of treatment by the insulinotropic peptide.

The insulinotropic peptide may be delivered over a period ranging from more than about one week to about one year or more, preferably for about one month to about a year or more, more preferably for about three months to about a year or more. The implantable, drug delivery device may include a reservoir having at least one orifice through which the insulinotropic peptide is delivered. The suspension formulation may be stored within the reservoir. In one embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005-0175701, 2007-0281024, and 2008-0091176).

The DUROS® delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a therapeutic agent at a predetermined rate based on the principle of osmosis. Extracellular fluid enters the DUROS® device through a semipermeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation of the present invention, comprising, for example, GLP-1(7-36) amide or exenatide, wherein the device is capable of delivering the suspension formulation to a subject over an extended period of time (e.g., about 3, about 6, or about 12 months) at a pre-determined, therapeutically effective delivery rate.

Implantable devices, for example, the DUROS® device, provide the following advantages for administration of a beneficial agent formulation: true zero-order release of the beneficial agent pharmacokinetically; long-term release period time (e.g., up to about 12 months); and reliable delivery and dosing of a beneficial agent.

Other implantable, drug delivery devices may be used in the practice of the present invention and may include regulator-type implantable pumps that provide constant flow, adjustable flow, or programmable flow of the compound, such as those available from Codman & Shurtleff, Inc. (Raynham, Mass.), Medtronic, Inc. (Minneapolis, Minn.), and Tricumed Medinzintechnik GmbH (Germany).

Implantable devices, for example, the DUROS® device, provide the following advantages for administration of the suspension formulations of the present invention: true zero-order release of the insulinotropic peptide pharmacokinetically; long-term release period time (e.g., up to about 12 months); and reliable delivery and dosing of the insulinotropic peptide.

The amount of beneficial agent employed in the delivery device of the invention is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl.

Typically, the osmotic delivery device is implanted within the subject, for example, subcutaneously. The device(s) can be inserted in either or both arms (e.g., in the inside, outside, or back of the upper arm) or into the abdomen. Preferred locations in the abdomen are under the abdominal skin in the area extending below the ribs and above the belt line. To provide a number of locations for insertion of one or more osmotic delivery device within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions.

The suspension formulation may also be delivered from a drug delivery device that is not implantable or implanted, for example, an external pump such as a peristaltic pump used for subcutaneous delivery in a hospital setting.

The suspension formulations of the present invention may also be used in infusion pumps, for example, the ALZET® (DURECT Corporation, Cupertino Calif.) osmotic pumps which are miniature, infusion pumps for the continuous dosing of laboratory animals (e.g., mice and rats).

The suspension formulations of the present invention may also be used in the form of injections to provide highly concentrated bolus doses of biologically active insulinotropic peptides.

In one embodiment of the present invention, the continuous delivery of, for example, derivatives and analogues of GLP-1 that have short-half lives after injection into humans (e.g., GLP-1(7-36) amide or exenatide) from an implantable device would be particularly beneficial. Further, the use of an implantable device, such as the DUROS® device, to deliver insulinotropic peptides could reduce injection-related side-effects and, with increased convenience of dosing, result in increased treatment compliance. The duration of drug delivery from one implant may be weeks or as long as one year.

Some advantages and benefits of the suspension formulations of the present invention delivered via an osmotic delivery device, such as a DUROS® device, include, but are not limited to the following. Increased treatment compliance can result in better efficacy and such increased compliance can be achieved using an implanted osmotic delivery device. Efficacy of treatment can be improved because an implantable osmotic device, such as a DUROS® device, can provide continuous and consistent delivery of drug (e.g., GLP-1 or exenatide) 24 hours per day to provide better control of blood glucose levels day and night. Further, it is believed that incretins and incretin mimetics may protect the beta cells in the pancreas and slow down the progression of type 2 diabetes mellitus. Twenty-four hour continuous and consistent drug delivery of incretins or incretin mimetics from the DUROS® device thus can provide even greater protection of the beta cells and may provide reversal of the disease progression. Continuous delivery of insulinotropic peptides (e.g., GLP-1 or exenatide) from the DUROS® device also allows treated subjects complete flexibility in planning meals and thus an increased quality of life compared to, for example, treatment with bolus injections that need to be timed relative to the major meals of the day. Also, unlike other sustained release formulations and depot injections, drug dosing when using a DUROS® device can be immediately halted by removal of the device, for example, if a safety issue arises for a particular subject.

In addition to GLP-1 derivatives and analogues demonstrating insulinotropic action, other derivatives of GLP-1 (e.g., GLP-1(9-36) amide) have been shown to reduce blood glucose by a mechanism that does not involve insulin secretion (Deacon, C. F., et al., Am. J. Physiol. Endocrinol. Metab. 282:E873-E879 (2002)). Further, GLP-1(9-36) amide has been shown to reduce postprandial glycemia independently of gastric emptying and insulin secretion (Meier, J. J., et al., Am. J. Physiol. Endocrinol. Metab. 290:E1118-E1123 (2006)). Accordingly, in another aspect, the present invention includes formulation of such GLP-1 derivatives into particles, suspension of the particles in a vehicle, and delivery of these suspension formulations to subjects to reduce blood glucose and/or to reduce postprandial glycemia essentially as described herein above for GLP-1 derivatives and analogues demonstrating insulinotropic action. In addition, GIP(3-42) appears to be a weak GIP receptor antagonist that does not exert insulin-related glucoregulation. Such GIP derivatives may also be formulated (singly or in combination with other peptides) following the guidance presented herein.

The present invention also includes methods of manufacturing the formulations of the present invention, including the particle formulations, suspension vehicles, and suspension formulations described herein above.

4.0.0 Suspension Formulation Uses

The suspension formulations as described herein provide promising alternatives to insulin therapy for subjects with diabetes mellitus. Diabetes mellitus type 2 or Type 2 Diabetes (also called non-insulin-dependent diabetes mellitus (NIDDM) or adult-onset diabetes) is a metabolic disorder that is primarily characterized by insulin resistance, relative insulin deficiency and hyperglycemia. The suspension formulations of the present invention, comprising insulinotropic peptides, are useful for stimulating insulin secretion, suppressing glucagon secretion, slowing gastric emptying, and possibly enhancing insulin sensitivity in peripheral tissues such as muscle and fat.

The suspension formulations of the present invention may be useful in the treatment of diabetes (e.g., diabetes mellitus, and gestational diabetes), and diabetic related disorders (e.g., diabetic cardiomyopathy, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia), as well as, hyperglycemia (e.g., related to treatment with medications that increase the risk of hyperglycemia, including beta blockers, thiazide diuretics, corticosteroids, niacin, pentamidine, protease inhibitors, L-asparaginase, and some antipsychotic agents), reducing food intake (e.g., treating obesity, controlling appetite, or reducing weight), stroke, lowering plasma lipids, acute coronary syndrome, hibernating myocardium, regulating gastrointestinal motility, and increasing urine flow.

In addition, the suspension formulations of the present invention may be potential regulators of appetite in subjects treated with the formulations.

In one embodiment, suspension formulations are administered using an osmotic delivery device as described above. Examples of target rates of delivery for suspension formulations of the present invention, comprising insulinotropic peptides, include, but are not limited to: suspension formulations comprising particle formulations comprising GLP-1 (e.g., GLP-1(7-36) amide), between about 20 μg/day and about 900 μg/day, preferably between about 100 μg/day and about 600 μg/day, for example, at about 480 μg/day; and suspension formulations comprising particle formulations comprising exenatide, between about 5 μg/day and about 320 μg/day, preferably between about 5 μg/day and about 160 μg/day, for example, at about 10 μg/day to about 20 μg/day. An exit sheer rate of the suspension formulation from the osmotic delivery device is determined such that the target daily target delivery rate of the insulinotropic peptide is reasonably achieved by substantially continuous, uniform delivery of the suspension formulation from the osmotic delivery device. Examples of exit sheer rates include, but are not limited to, about 1 to about $1 \times 10^{-7}$ reciprocal second, preferably about $4 \times 10^{-2}$ to about $6 \times 10^{-4}$ reciprocal second, more preferably $5 \times 10^{-3}$ to $1 \times 10^{-3}$ reciprocal second.

A subject being treated with the suspension formulations of the present invention may also benefit from co-treatment with other agents (e.g., sulfonylureas, meglitinides (e.g., repaglinide, and nateglinide), metformin, and combinations of such agents), alpha glucosidase inhibitors, amylin (as well as synthetic analogues such as pramlintide), dipeptidyl peptidase IV (DPP-IV) inhibitors (e.g., sitagliptin and vildagliptin), and long/short acting insulins.

Use of oral dipeptidyl peptidase-IV (DPP-IV or DPP-4) inhibitors orally to prevent cleavage of GLP-1 may be particularly useful when the suspension formulation of the present invention comprises a GLP-1 variant that is cleavable by dipeptidyl peptidase-IV (see, e.g., U.S. Pat. No. 7,205,409).

Example 5 presents data demonstrating that delivery of a formulation comprising exenatide using the DUROS® device resulted in decreased glucose levels and weight loss in treated animals.

Other objects may be apparent to one of ordinary skill upon reviewing the following specification and claims.

EXPERIMENTAL

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the specifications for content and purity required of pharmaceutical products.

Example 1

Exenatide Particle Formulations

This example describes making exenatide particle formulations.

A. Formulation 1.

Exenatide (0.25 g) was dissolved in 50 mM sodium citrate buffer at pH 6.04. The solution was dialyzed with a formulation solution containing sodium citrate buffer, sucrose, and methionine. The formulated solution was then spray dried using Buchi 290 with 0.7 mm nozzle, outlet temperature of 75° C., atomization pressure of 100 Psi, solid content of 2%, and flow rate of 2.8 mL/min. The dry powder contained 21.5% of exenatide with 4.7% residual moisture and 0.228 g/ml density.

B. Formulations 2 and 3.

Two additional formulations of exenatide were prepared essentially by the method just described. Following here in Table 3 is a summary of the weight percentages (wt %) of the components of the Formulations 1, 2 and 3.

TABLE 3

| Component | Particle Formulation 1 (wt %) | Particle Formulation 2 (wt %) | Particle Formulation 3 (wt %) |
| --- | --- | --- | --- |
| Exenatide | 21.5 | 11.2 | 50.0 |
| Sodium Citrate* | 63.6 | 74.7 | 28.4 |
| Citric Acid* | 7.1 | 9.1 | 3.6 |
| Sucrose | 3.9 | 2.5 | 9.0 |
| Methionine | 3.9 | 2.5 | 9.0 |

*Sodium Citrate/Citric Acid formed the citrate buffer for this particle formulation.

Example 2

GLP-1 Dry Powder

This example describes making an GLP-1(7-36) amide particle formulation. GLP-1(7-36) amide (1.5 g) was dissolved in 5 mM sodium citrate buffer at pH 4. The solution was dialyzed with a formulation solution containing sodium citrate buffer and methionine. The formulated solution was then spray dried using Buchi 290 with 0.7 mm nozzle, outlet temperature of 70° C., atomization pressure of 100 Psi, solid content of 1.5%, and flow rate of 5 mL/min. The dry powder contained 90% of GLP-1(7-36) amide.

Example 3

Exenatide Suspension Formulation

This example describes making suspension formulations comprising a suspension vehicle and an exenatide particle formulation.

A. Suspension Formulation of 20 wt % Exenatide Particles.

An exenatide particle formulation was generated by spray-drying, and contained 20 wt % exenatide, 32 wt % sucrose, 16 wt % methionine and 32 wt % citrate buffer.

A suspension vehicle was formed by dissolving the polymer polyvinylpyrrolidone in the solvent benzyl benzoate at approximately a 50/50 ratio by weight. The vehicle viscosity was approximately 12,000 to 18,000 poise when measured at 33° C. Particles containing the peptide exenatide were dispersed throughout the vehicle at a concentration of 10% particles by weight.

B. Suspension Formulations of Particle Formulations 1, 2, and 3.

A suspension vehicle was formed by dissolving the polymer polyvinylpyrrolidone K-17 (typically having an approximate average molecular weight range of 7,900-10,800) in the solvent benzyl benzoate heated to approximately 65° C. under a dry atmosphere and reduced pressure at approximately a 50/50 ratio by weight. The vehicle viscosity was approximately 12,000 to 18,000 poise when measured at 33° C. Particle formulations 1-3, described in Example 1, were dispersed throughout the vehicle at the concentrations (by weight percent) shown in Table 4.

TABLE 4

| Component | Suspension Formulation 1 (wt %) | Suspension Formulation 2 (wt %) | Suspension Formulation 3 (wt %) |
|---|---|---|---|
| Particle Formulation 1 | 21.40 | — | — |
| Particle Formulation 2 | — | 11.73 | — |
| Particle Formulation 3 | — | — | 10.05 |
| Polyvinylpyrrolidone | 39.30 | 44.13 | 44.98 |
| Benzyl Benzoate | 39.30 | 44.13 | 44.98 |

Example 4

GLP-1(7-36) amide Formulation

This example describes making a suspension formulation comprising a suspension vehicle and an GLP-1(7-36) amide particle formulation. A GLP-1(7-36) amide particle formulation was generated by spray-drying, and contained 90 wt % GLP-1, 5 wt % methionine and 5 wt % citrate buffer.

A suspension vehicle containing the polymer polyvinylpyrrolidone was dissolved in the solvent benzyl benzoate at approximately a 50/50 ratio by weight. The vehicle viscosity was approximately 12,000 to 18,000 poise when measured at 33° C. Particles containing the peptide GLP-1(7-36) amide were dispersed throughout the vehicle at a concentration of 33% particles by weight.

Example 5

Continuous Delivery of Exenatide Using the DUROS® Device Resulted in Decreased Glucose Levels and Weight Loss in Treated Animals The data in this Example demonstrated the effect of continuous and consistent delivery of an exenatide formulation from the DUROS® device on glucose levels and weight in the Zucker Diabetic Fatty (ZDF) rat model of type 2 diabetes.

The ZDF rat model has been previously described as an accurate model for Type 2 diabetes based on impaired glucose tolerance caused by the inherited obesity gene mutation which leads to insulin resistance (see, e.g., Clark, J., et al., *Proc. Soc. Exp. Biol. Med.* 173: 68-75 (1983); Peterson, R. G., et al., *ILAR News* 32: 16-19 (1990); Peterson, R. G., In *Frontiers in Diabetes Research. Lessons from Animal Diabetes III*, edited by E. Shafrir, pp. 456-458. London: Smith-Gordon (1990); Vrabec, J. T., *Otolaryngol. Head Neck Surg* 118: 304-308 (1998); Sparks, J. D., et al., *Metabolism* 47: 1315-1324 (1998)).

The study design presented in Table 5 was used.

TABLE 5

| Group | Treatment (mcg*/day) | ZDF Rate Type | Number of Males |
|---|---|---|---|
| 1 | Control | Obese | 6 |
| 2 | 20 | Obese | 6 |
| 3 | 20 | Lean | 6 |

*micrograms

Rats (Group 2, obese, and Group 3, lean, n=6/group) in treatment groups were exposed to 20 mcg/day of exenatide (Suspension Formulation 2; Example 3, Table 4) continuously delivered using DUROS® devices for seven 24 hour periods (wherein the device was inserted on day 1 and removed on day 8), while placebo devices were inserted into rats in the control group (Group 1; n=6). The DUROS® devices were inserted subcutaneously into each of the animals.

Over the treatment period the following endpoints were evaluated. Clinical signs/Mortality were assessed at least once daily. Body weight was determined prior to implantation, daily during the observation period, and at termination. Blood glucose was determined as follows: fasted blood samples collected on Days-1 and 8; and un-fasted blood samples were taken three times each day (4-6 hours apart) Days-1 and 8, with two un-fasted blood samples taken on Days-1 and 8. Blood glucose was determined using a One-Touch Ultra® (Johnson & Johnson, New Brunswick N.J.) blood glucose meter. Glucose levels were measured three times per day. Quantitative HbAlc was determined for fasted blood samples collected on Days-1 and 8 using a DCA 2000 Plus Analyzer (GMI, Inc., Ramsey Minn.). Serial blood samples were obtained pre-Implant (0), at 12, 24, 36, 48, 72 hours and at Days 5 and 7 after implantation. These samples were centrifuged, the plasma harvested, and stored at −70° C. Necropsy included macroscopic examination performed on Day 8 of the observation period.

Figure 2:
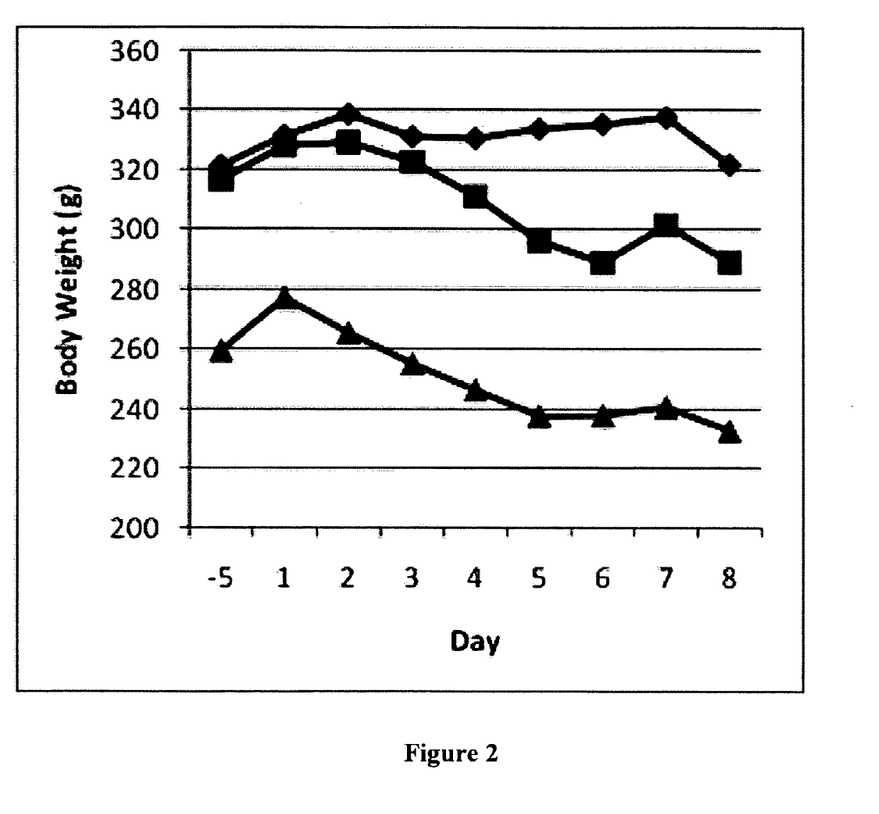
FIG. 2 presents data for group mean body weights of test animals treated by continuous delivery of exenatide from a DUROS® (ALZA Corporation, Mountain View Calif., licensed to Intarcia Therapeutics, Inc., Hayward Calif.) device. In the figure, the vertical axis is mean body weight in grams (Body Weight (g)) and the horizontal axis is the day (Day). The obese animals of Group 1 (closed diamonds) were the control group to which 0 mcg of exenatide from a DUROS® device was administered per day. The animals of Group 2 (closed squares) were obese animals to which 20 mcg of exenatide from a DUROS® device was administered per day. The animals of Group 3 (closed triangles) were lean animals to which 20 mcg of exenatide was administered per day.

FIG. 2 presents the data obtained for group mean body weights (in grams). Decreased body weight was observed in both obese (FIG. 2; closed squares) and lean (FIG. 2; closed triangles) rats treated with exenatide by Day 4 (Obese: Day 1=329±15.2 g versus Day 4=296.2±14.2 g (p<0.01); and lean: Day 1=265.4±9.1 g versus Day 4=237.6±7.8 g (p<0.01)). Overall, there was a 10.7% weight loss in obese treated rats and a 15.1% weight loss in lean treated rats by Day 6. In contrast, obese rats with placebo devices (FIG. 2; closed diamonds) showed a slight increase (1.8%) in body weight by Day 6.

Figure 3:
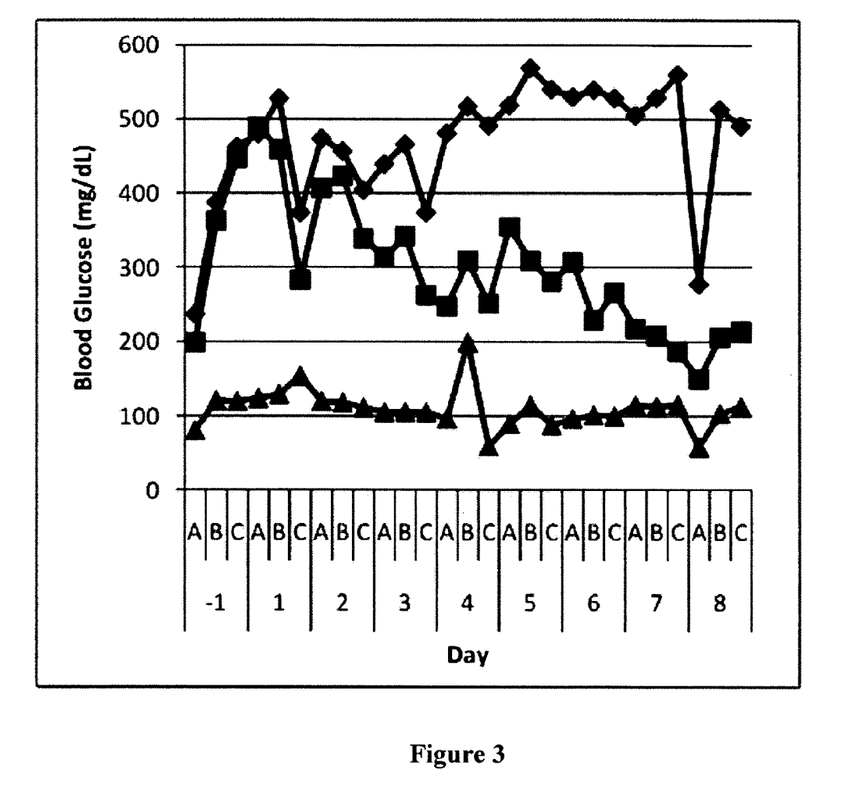
FIG. 3 presents data for group mean blood glucose concentrations of test animals treated by continuous delivery of exenatide from a DUROS® device. In the figure, the vertical axis is mean blood glucose in mg/dL (Blood Glucose (mg/dL)) and the horizontal axis is the day (Day), wherein each day has three associated blood glucose values (A, B, C). Day-1A is a fasting blood glucose value and Day 8A is a fasting blood glucose value. The obese animals of Group 1 (closed diamonds) were the control group to which 0 mcg of exenatide was administered per day. The animals of Group 2 (closed squares) were obese animals to which 20 mcg of exenatide from a DUROS® device was administered per day. The animals of Group 3 (closed triangles) were lean animals to which 20 mcg. of exenatide from a DUROS® device was administered per day.

FIG. 3 presents the data obtained for group mean blood glucose concentrations (in mg/dL). Decreased blood glucose levels were apparent in obese treated rats (FIG. 3; closed squares) compared to obese controls (FIG. 3; closed diamonds) within 1 day after DUROS® device insertion. Starting at Day 3 mean glucose levels in obese treated rats were 163±92 mg/dL, while obese control rats were 481±47 mg/dL (p<0.05). Between Days 3-7, obese rats treated with 20 mcg/day of exenatide had decreased blood glucose levels that approached those in lean animals, while placebo-treated obese rats had mean glucose levels of 502 mg/dL. Lean animals (FIG. 3; closed triangles) were consistently around glucose levels of 100 mg/dL. A glucose level of 100 mg/dL is considered to be normal.

Figure 4:
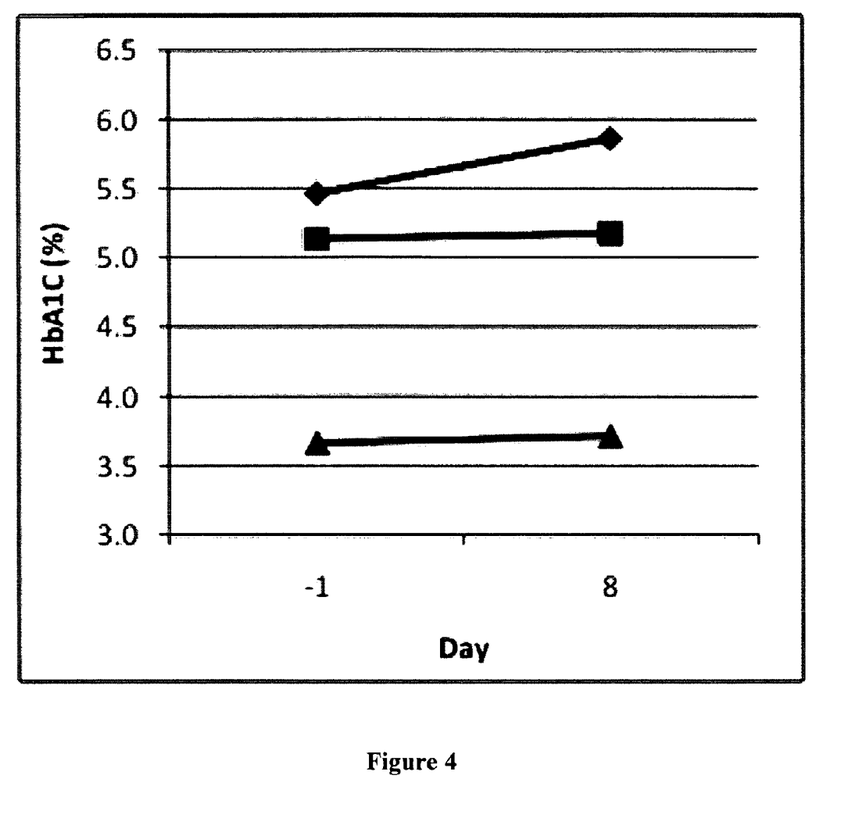
FIG. 4 presents data for group mean HbAlc values of test animals treated by continuous delivery of exenatide from a DUROS® device. In the figure, the vertical axis is mean percent HbAlc (HbAlc (%)) and the horizontal axis is the day (Day). The obese animals of Group 1 (closed diamonds) were the control group to which 0 mcg of exenatide was administered per day. The animals of Group 2 (closed squares) were obese animals to which 20 mcg of exenatide was administered per day. The animals of Group 3 (closed triangles) were lean animals to which 20 mcg of exenatide from a DUROS® device was administered per day.

FIG. 4 presents the data obtained for group mean blood HbA1c values. Treated obese rats (FIG. 4; closed squares) showed an overall increase of 5.8% in HbA1c levels, while obese control rats (FIG. 4; closed diamonds) showed an increase of 6.7% over the study period. Even though there was a decrease of mean blood glucose concentrations over time for the treated obese rats there did not appear to be a corresponding decrease in HbA1c in these animals. This result is likely because the study was not long enough as HbA1c levels are proportional to average blood glucose concentrations over one to two month periods.

These data demonstrated that continuous, uniform delivery of exenatide resulted in glucose-lowering together with a potent effect on body weight in treated animals. These results support the use of the DUROS® device for long-term steady state dosing of incretin mimetics, for example, a suspension formulation comprising exenatide, in the treatment of human diabetes.

As is apparent to one of skill in the art, various modification and variations of the above embodiments can be made without departing from the spirit and scope of this invention. Such modifications and variations are within the scope of this invention.

What is claimed is:

1. A suspension formulation suitable for use in an osmotic delivery device comprising,
   a particle formulation comprising an insulinotropic peptide, a disaccharide, methionine, and a buffer; and
   a non-aqueous, single-phase suspension vehicle that consists essentially of about 20 wt % to about 60 wt % benzyl benzoate and about 80 wt % to about 40 wt % polyvinylpyrrolidone, the suspension vehicle having a viscosity of between about 12,000 to about 18,000 poise at 33° C.;
   wherein the suspension vehicle exhibits viscous fluid characteristics, and the particle formulation is dispersed in the vehicle.

2. The formulation of claim 1, wherein the insulinotropic peptide is a glucagon-like peptide-1 (GLP-1), a derivative of GLP-1, or an analogue of GLP-1.

3. The formulation of claim 2, wherein the insulinotropic peptide is GLP-1(7-36) amide.

4. The formulation of claim 1, wherein the insulinotropic peptide is exenatide, a derivative of exenatide, or an analogue of exenatide.

5. The formulation of claim 4, wherein the insulinotropic peptide is exenatide having the amino acid sequence of SEQ ID NO:2.

6. The formulation of claim 1, wherein the buffer is selected from the group consisting of citrate, histidine, succinate, and mixtures thereof.

7. The formulation of claim 6, wherein the buffer is a citrate buffer.

8. The formulation of claim 1, wherein the disaccharide is selected from the group consisting of lactose, sucrose, trehalose, cellobiose, and mixtures thereof.

9. The formulation of claim 1, wherein the particle formulation is a spray dried preparation of particles.

10. The formulation of claim 1, wherein the vehicle is about 50% solvent and about 50% polymer.

11. The formulation of claim 1, wherein the suspension formulation has an overall moisture content of less than or equal to about 10 wt %.

12. An osmotic delivery device, comprising the suspension formulation of claim 1.

13. A method of manufacturing an osmotic delivery device comprising, loading the suspension formulation of claim 1 into a reservoir of the osmotic delivery device.

14. A method of treating type II diabetes in a subject in need of such treatment, comprising delivering the suspension formulation of claim 1 from an osmotic delivery device at a substantially uniform rate for a period of about one month to about a year.

15. The method of claim 14, wherein the insulinotropic peptide is GLP-1(7-36) amide and delivering the suspension formulation is at a substantially uniform rate of between about 100 μg/day and about 600 μg/day.

16. The method of claim 14, wherein the insulinotropic peptide is exenatide and delivering the suspension formulation is at a substantially uniform rate of between about 5 μg/day and about 160 μg/day.

* * * * *